United States Patent [19]
Yonemura

[11] Patent Number: 5,401,663
[45] Date of Patent: Mar. 28, 1995

[54] REAGENT FOR COAGULATING BLOOD

[75] Inventor: Masaru Yonemura, Kobe, Japan

[73] Assignee: Toa Medical Electronics Co., Ltd., Kobe, Japan

[21] Appl. No.: 154,399

[22] Filed: Nov. 18, 1993

Related U.S. Application Data

[63] Continuation of Ser. No. 892,965, Jun. 3, 1992, abandoned.

[30] Foreign Application Priority Data

Aug. 30, 1991 [JP] Japan .................................. 3-246740

[51] Int. Cl.$^6$ .............................................. G01N 33/86
[52] U.S. Cl. ...................................... 436/69; 436/16; 436/18; 436/71; 435/2; 435/13; 435/214; 252/408.1; 530/381; 530/382; 530/384
[58] Field of Search ................. 436/16, 18, 69, 71; 435/2, 13, 214; 252/408.1; 530/381, 384, 382

[56] References Cited

U.S. PATENT DOCUMENTS

| | | | |
|---|---|---|---|
| 2,847,347 | 8/1958 | Singher et al. | 435/13 |
| 3,980,432 | 9/1976 | Trobisch et al. | 435/13 |
| 3,983,004 | 9/1976 | Trobisch et al. | 436/18 |
| 4,067,964 | 1/1978 | Schwinn et al. | 424/105 |
| 4,264,471 | 4/1981 | Briggs | 252/408.1 |
| 4,501,731 | 2/1985 | Tishkoff et al. | 424/101 |
| 4,637,932 | 1/1987 | Pancham | 424/101 |
| 4,692,406 | 9/1987 | Becker et al. | 436/69 |
| 4,755,461 | 7/1988 | Lawson et al. | 436/69 |
| 4,784,944 | 11/1988 | Koide | 436/69 |
| 4,880,788 | 11/1989 | Moake et al. | 514/150 |
| 5,043,425 | 8/1991 | Aoki et al. | 530/350 |
| 5,190,919 | 3/1993 | Fair et al. | 514/15 |

Primary Examiner—Robert J. Warden
Assistant Examiner—N. Bhat
Attorney, Agent, or Firm—Jones, Tullar & Cooper

[57] ABSTRACT

A reagent blood coagulation that causes an increase in turbidity changes when added to a plasma sample containing a substance activating coagulation factor activating such as tissue thromboplastin, phospholipid and thrombin, calcium ion, and molecular substance such as high molecular vinyl and a high molecular polysaccharide. By adding a molecular substance to the reagent, the turbidity change due to blood coagulation is increased, and hence the changing quantity of transmitted light or scattered light increases, thereby making it possible to achieve a more accurate detection. Besides, by adjusting the electric conductivity, pH and osmotic pressure to proper values, the turbidity change due to blood coagulation may be further amplified.

12 Claims, 6 Drawing Sheets

REAGENT FOR COAGULATING BLOOD

This is a continuation of copending application Ser. No. 07/892,965 filed on Jun. 3, 1992 now abandoned.

BACKGROUND OF THE INVENTION

The invention relates to a reagent for coagulating blood and for measuring the coagulating activity of a plasma specimen by using optical measuring apparatus or viscosity detecting apparatus, and more particularly to a reagent for coagulating blood and an apparatus capable of measuring specimen of low coagulating activity, while contributing to enhancement of accuracy in ordinary specimens, By preparing them into a composition so that a larger than ever optical changing quantity or viscosity changing quantity may be obtained.

The mechanism of blood coagulation is explained by reference to FIG. 1. The mechanism of blood coagulation usually occurs in two pathways. One route is called the extrinsic coagulation, in which starting from the tissue thromboplastin released from epidermic cell or the like, the coagulated VII factor is activated, and by this activated coagulated VII factor, the coagulated X factor is activated, being followed by activation of the coagulated V factor, II factor, and finally fibrinogen is transformed into fibrin to induce coagulation.

The other route is called the intrinsic coagulation, in which the coagulated XII factor is activated by contact or the like to activate the XI factor. In succession, the activated XI factor activates the IX factor, and further the activated IX factor activates the X factor by collaborating action with calcium ions and VIII factor. It is later followed by activation of the V factor and II factor, and finally fibrinogen is transformed into fibrin to induce coagulation.

Methods for detecting blood coagulation may be roughly classified into the method of increasing viscosity of liquid along with coagulation of blood (viscosity detecting method), the method of detecting white turbidity along with coagulation of blood (turbidity detecting method), and their combined method. In the viscosity detecting method, bar-shaped or spherical magnetic matter is injected into the plasma specimen, and this is mixed with a reagent for detecting coagulation, and the motion of the magnetic matter becomes dull due to coagulation, which is detected. This viscosity detecting method, however, largely differs in the resulting measurements depending on the shape of the fibrin lumps which are final products of blood coagulation (that is, the quantity of fibrin or stiffness of coagulated state), and its fatal defect is that it is impossible to detect unless the viscosity is higher than a specific level. Besides, because of the measuring principle of observing the motion of magnetic matter, the measurement is affected by the intensity of magnetic matter.

The turbidity detecting method measures coagulation only by mixing the plasma specimen and coagulating reagent, and it does not require magnetic matter or other charging. This method of detection is available in the transmitted light detecting method and scattered light detecting method. In these methods of detection, if the fibrinogen quantity is small, the change of the transmitted light quantity or the scattered light quantity can be detected, and it is hence free from the shortcoming known in the viscosity detecting method. However, in either detecting method, it is quite natural that detection is more accurate if the changing quantity of light is greater, and the coagulating reagent to be used desirably has such a characteristic as to express the changing quantity of light very largely.

FIG. 2 is a diagram which explains the change of signal intensity obtained in the scattered light detecting method. The result of investigating the plasma coagulating process by an optical detecting device (scattered light detecting method) is shown. In the diagram, point A is the moment at which mixing of the plasma and coagulating reagent occurs, and afterwards the coagulation reaction progresses in multiple steps, and as a stable fibrin is formed, a change in scattered light appears (point B in the diagram). As the formation of stable fibrin progresses, the change of scattered light increases, but most fibrinogen is consumed, and the change of quantity of scattered light decreases, and the reaction terminates (point C). The coagulating time may be, for example as disclosed in Japanese Laid-open Patent Sho. 59-203959, determined as time T until reaching the 50% scattered light quantity supposing the quantity of scattered light at time B to be 0% and the quantity of scattered light at time C to be 100%. Incidentally $\Delta H$ is the changing quantity of scattered light from the start of the coagulation reaction until its end.

To measure the extrinsic coagulation pathway, the method known as Quick's single-stage method is most popular at the present. This measurement (examination) is generally called the PT (prothrombin time) method, which is capable of not only comprehensively measuring the activity of extrinsic coagulating factors, but also measuring individual extrinsic coagulating factors by using coagulating factor deficient plasma. Today, in the patients administered anticoagulants (such as warfarin) for the treatment of heart disease, this measuring method is important as the means for monitoring the effect of anticoagulants.

Most reagents used in this method are prepared by grinding rabbit brain in the presence of acetone, dehydrating, drying and extracting tissue thromboplastin. The tissue thromboplastin differs in reactivity to extrinsic coagulating factors or yield depending on the extraction conditions, and various methods of extraction have so far been invented. For example, Ronald Bach et al. attempted to enhance the yield by solubilizing the tissue thromboplastin by using a surface active agent (Triton X-100) (The J. Biological Chemistry, Vol. 256, No. 16, pp. 8324–8331, 1981). As a similar method, in Japanese Patent Publication Sho. 63-56501, it is proposed to use a surface active agent of the cholic acid group at the time of tissue thromboplastin extraction, and concerning these methods, M. Hvatum and H. Prydz (Biochimica et Biophysica Acta, Vol. 130, pp. 92–101, 1966) and H. Gonmori and Takeda (Thrombos. Haemostas. Vol. 36, pp. 90–130, 1976) reported the method of preparing tissue thromboplastin in detail in their papers. Besides, Japanese Patent Publication Sho. 58-43080 discloses an invention for preparing a useful tissue thromboplastin by maintaining the pH during extraction at the alkaline side.

Whichever method of extraction is selected, it is indispensable to contain tissue thromboplastin in the reagent used in the inspection method (prothrombin time method) known at Quick's single-stage method, and at the same time the tissue thromboplastin must be uniform in the reactivity to extrinsic coagulating factors and must finally possess the action of transforming fibrinogen into fibrin.

For the conventional reagent for coagulating blood (hereinafter called PT reagent), it was the ultimate requirement to have an accurate reactivity to extrinsic coagulating factors and a capability of finally forming fibrin. Little attention was paid to the display of accurate measurement results. Accordingly, significant fluctuations of result of examination about coagulation was allowed.

The problem that the invention is to solve is to prepare such a composition as to enlarge the optical changing quantity in order to display the result of measurements accurately. As a result, not only can a specimen of low coagulating activity be measured, but the invention also contributes to accuracy enhancement in normal specimens.

OBJECT AND SUMMARY OF THE INVENTION

It is hence a primary object of the invention to provide a reagent for coagulating blood which is capable of increasing the optical changing quantity and viscosity changing quantity.

To achieve the above object, the reagent for coagulating blood according to the invention comprises a substance activating coagulating factor, calcium ion, and a high molecular substance.

As a substance activating coagulating factor, a substance selected from the following is used Examples of a reagent containing a substance activating coagulating factor are as follows:

(a) Reagent containing tissue thromboplastin

Prothrombin time reagent, reagent for measuring protein induced by vitamin K (reagent for measuring complex factor)

(b) Reagent containing phospholipid

Partial thromboplastin time reagent, activated partial thromboplastin time reagent (c) Reagent containing thrombin Reagent for measuring fibrinogen, AT-III measuring reagent It is hence a feature of the invention that the substance activating coagulating factor is a substance selected from the group consisting of tissue thromboplastin, phospholipid and thrombin.

An example of a reagent containing tissue thromboplastin is explained below. To prepare a reagent containing tissue thromboplastin, tissues (brain, lung, placenta, etc.) of mammal animals (human, rabbit, cattle, horse, monkey, etc.) are treated with acetone to obtain acetone treated powder (hereinafter called acetone powder), and fractions containing tissue thromboplastin are extracted from the acetone powder, and calcium ions and high molecular substances are added in the fractions.

An example of a manufacturing process is illustrated.

I. The brain of a rabbit is taken out.

II. Preparation of acetone powder

The rabbit brain is mixed and ground in acetone. The mixture is filtered and dried.

III. Removal of blood components and foreign proteins

The acetone powder is mixed in an acidic solution (for example, hydrochloric acid water), and is centrifuged to obtain a sediment fraction. At this time, the floating fraction contains blood components and foreign proteins.

IV. Extraction of tissue thromboplastin

The sediment fraction is mix ed and stirred in solution, for extracting (for example a solution containing sodium formate or sodium acetate) and centrifuged, and a floating fraction containing tissue thromboplastin is collected.

V. Addition of high molecular substances

Calcium ions and high molecular substances are added to the fraction containing tissue thromboplastin.

VI. Freeze-drying

The above reagent is freeze-dried.

At step II, meanwhile, it is desired to mix the rabbit brain and acetone at a ratio by weight of 1:7. The acetone powder is commercially available and may be bought.

At step III, by mixing acetone powder with an acidic solution (such as hydrochloric acid water), the undesired component may be much eluted in the solution, so that the removal rate of the undesired component may be enhanced (blood corpuscles hemolyze in acidity).

At step IV, by using as the solution for extracting sodium formate or sodium acetate at a concentration of 25 to 250 mM, a tissue thromboplastin of high coagulating activity may be obtained efficiently.

The high molecular substances at step V may include, among others, high molecular vinyl selected from the group comprising polyethylene glycol, polyvinyl alcohol, and polynoxylene, or high molecular polysaccharide selected from the group comprising agarose, soluble starch, glycogen, dextran and dextrin. As the high molecular substance, either high molecular vinyl or high molecular polysaccharide, or both may be used. More specifically, for example, polyethylene glycol with a molecular weight of 1,000 to 500,000 (more preferably 5,000 to 100,000, most preferably 20,000), or dextran with a molecular weight of 5,000 to 2,000,000 (more preferably, 50,000 to 500,000, or most preferably 170,000 to 220,000) may be preferred. The content may be properly determined, but it is generally at 0.25% to 2.0% (w/v), being that the effect of high sensitivity is not obtained if the content is too little, or the reaction performance deteriorates due to excessive viscosity if it is too much.

After adding the high molecular substance, by setting the reagent in the state at least satisfying one of the following conditions 1 to 3, a reagent of a higher sensitivity will be obtained (best when all three conditions are satisfied).

1. The electric conductivity is adjusted in the range of 4.0 to 15 mS (more preferably in the range of 6.5 to 11.0 mS).

2. The pH is adjusted in the range of 6.7 to 8.2 (more preferably in the range of 7.2 to 7.5).

3. The osmotic pressure is adjusted in the range of 100 to 700 mOsm/kg (more preferably in the range of 350 to 700 mOsm/kg).

For adjustment of the electrical conductivity, an electrolyte may be used (such as salt). For adjustment of the pH, acid or alkali is used (e.g. hydrochloric acid, sodium hydroxide). For adjustment of the osmotic pressure, a substance which is non-electrolytic and water-soluble at the same time is used (e.g. sugar, urea). The prepared thromboplastin reagent should be preferably freeze-dried so that it can be stored for a long period. Before use, the dry powder is dissolved in a specific amount of water to return to an initial state of solution.

It is thus preferred in the invention to use, as the substance activating coagulating factor, a fraction containing tissue thromboplastin taken out from the acetone treated powder obtained by treating mammal tissues with acetone. The fraction containing tissue thromboplastin is preferably obtained by dissolving the acetone treated powder in solution, mixing, stirring and centrifuging, or by floating the acetone treated powder in an acidic liquid, removing blood components and foreign proteins by centrifugation, adding liquid to the sediment fraction, stirring and then centrifuging.

The reagent containing tissue thromboplastin is described above, while the reagent containing phospholipid or the reagent containing thrombin may be obtained by employing the known art. Or as the reagent containing tissue thromboplastin, the prothrombin time reagent (PT reagent, the reagent for comprehensively measuring the extrinsic coagulation reaction in FIG. 1) is distributed by DADE, ORTHO, GD, all of the United States, Bering and BM, both of Germany, and others. As the reagent for measuring the activity of vitamin K derived enzyme (reagent for measuring complex factor), Thrombo Test and Hepaplastin Test (both tradenames) are distributed by Eisai of Japan, and Complex Factor H and Complex Factor T (both tradenames) are distributed by Kokusai Shiyaku of Japan.

As the reagent containing phospholipid, the APTT reagent and PTT reagent (the reagent for comprehensively measuring the intrinsic coagulation reaction in FIG. 1) are distributed by DADE, ORTHO, GD, all of the United States, Bering and BM, both of Germany, and others.

As the reagent containing thrombin, the reagent for measuring fibrinogen, reagent for measuring thrombin time, or reagent for measuring AT-III are distributed by DADE, ORTHO, GD, all of the United States, Bering and BM, both of Germany, Kokusai Shiyaku of Japan, and others.

Therefore, in the invention, as the substance activating coagulating factor, the phospholipid containing fraction obtained from acetone treated powder prepared by treating mammal tissue with acetone, or the thrombin containing fraction refined from plasma of mammal may be used.

By mixing the blood coagulation reagent of the invention in the plasma, coagulation factors in the plasma are activate one after another, and finally fibrinogen is transformed into fibrin to terminate the coagulation reaction. In the final process, first monomers of fibrin are formed, and the monomers are gradually polymerized to form polymer (fibrous), so that the fibrin become fibrous. As the fibrin fibers are entangled like a mesh, the mixed solution becomes turbid and is gelled.

By tracing the optical characteristics (for example, intensity of scattered light) of the mixed solution sequentially from the point of mixing the reagent, the time until the end of coagulation is known, from which the ability to coagulate is calculated.

The reagent of the invention contains high molecular substance. By the coexistence of the fiber and high molecular substance, the entangling is more complicated, and the difference in the optical characteristic between right after mixing the reagent (before coagulation) and after the coagulation reaction is greater than before (that is, higher in sensitivity).

Besides, by varying the electric conductivity, pH or osmotic pressure, the quantity of the optical change varies. By setting these values at proper values, a higher sensitivity is expected.

Thus, when the reagent of the invention is mixed with the specimen plasma, the coagulation factors in the plasma are sequentially activated, and finally the fibrinogen is transformed into fibrin. At this time, for example, by detecting the turbidity change (increase of turbidity) optically, the coagulation time is measured, from which the the ability to coagulate is assessed (calculated).

In the final process of blood coagulation, the fibrinogen is transformed into fibrin, but initially monomers of fibrin are formed. As the reaction is advanced, the fibrin monomers grown into dimer and further into polymer (fiber) by a polymerization reaction. In this process, the greater the quantity of fibers (fibrin) and the more complicated is the fiber entanglement, the greater is the turbidity change, and therefore measurement of the ability to coagulate is enhanced in both accuracy and reproducibility. The blood coagulation reagent of the invention contains a high molecular substance in order to cause a greater change in turbidity, and therefore it increases the hardness of coagulation owing to entangling of fibers and the high molecular substance, as well as entangling of fibers; and amplifies the optical change quantity. Besides, by properly controlling conditions, such as electrical conductivity, the polymerization reaction from fibrin monomers to fibrin polymer may be encouraged. It is anyway effective to increase the turbidity change due to blood coagulation, so that a reagent of high sensitivity may be prepared.

DETAILED DESCRIPTION OF THE PREFERRED EMBODIMENTS

Figure 1:
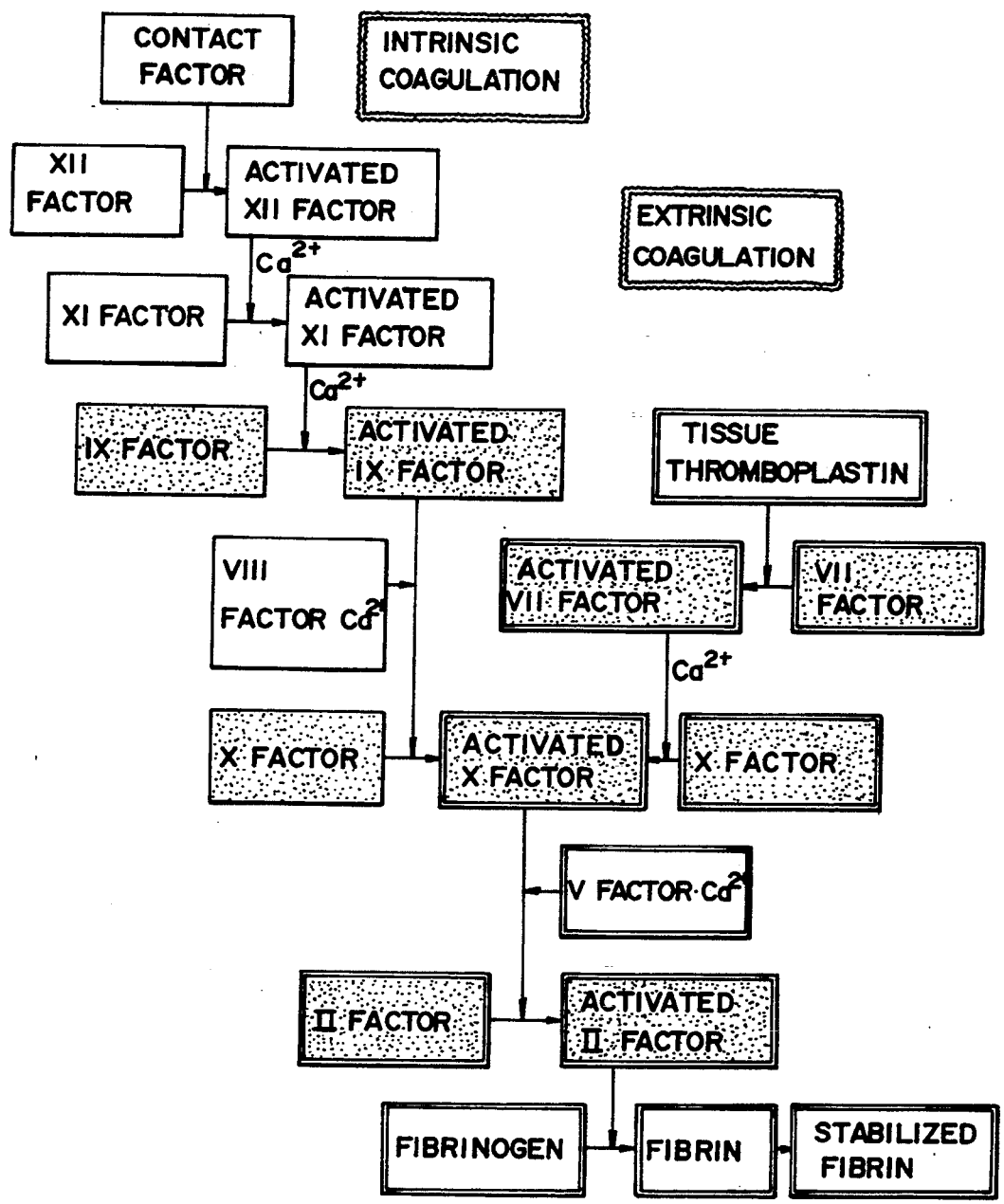
FIG. 1 is a block diagram showing the known general mechanism of blood coagulation.
Figure 2:
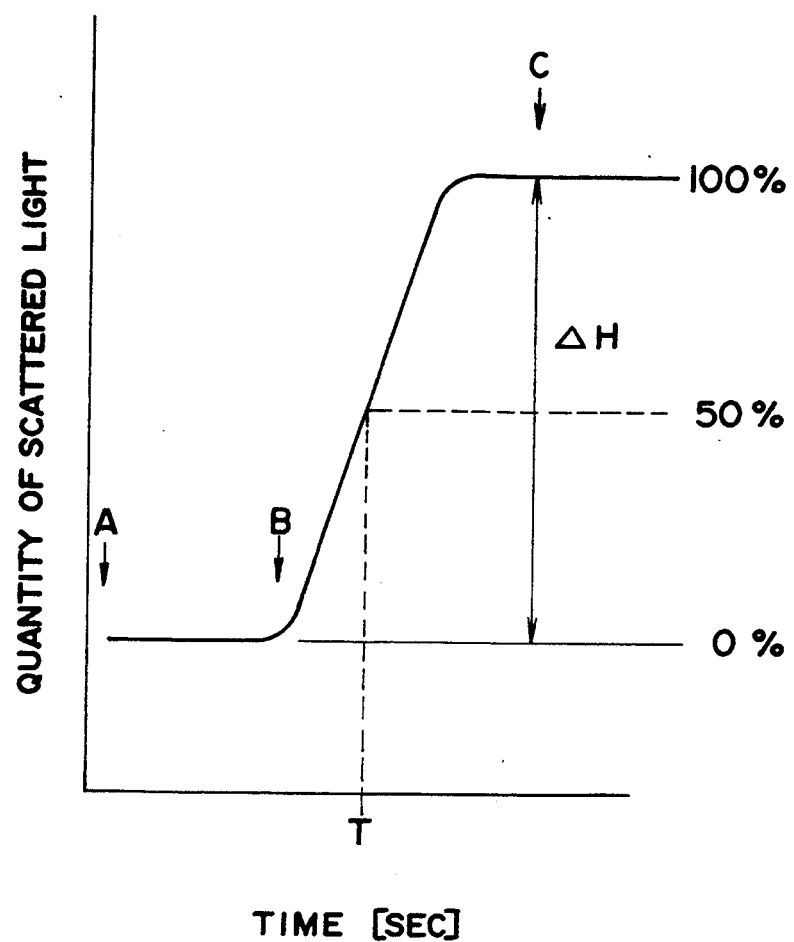
FIG. 2 is a graph showing tie relation between change of signal and blood coagulation obtained by the conventional method of detecting scattered light.

For the reagent used in the method of examination called Quick's single-stage method (prothrombin time method), it is indispensable to contain tissue thromboplastin in order to endow the extrinsic coagulation factors with reactivity; and moreover in order that the resulting reaction be measured accurately, it is necessary to set the reaction environments so that the coagulation lumps may be firmer. Accordingly, in a preferred embodiment, tissue thromboplastin of high reactivity was extracted from rabbit brain tissues in the following manner:

(1) The rabbit was anesthetized with chloroform or other anesthetic, and whole blood was extracted from the cervical artery. From the brain artery, normal (physiological) saline was perfused to rinse the blood in the brain. Then the cranium was opened, and the brain was removed (picked out).

(2) To 100 g of rabbit brain obtained in this way, 700 ml of cold acetone was mixed, and the brain was ground and stirred by a mixer, and dehydrated and pulverized. The ground matter was filtered and dried in a vacuum, and the acetone powder (AP) was obtained.

(3) 10 g of AP was mixed in 100 ml of hydrochloric acid water (0.02 normal), and was centrifuged (3,000 rpm×30 min) to collect sediment fractions. The separated and removed floating fractions contained blood components and foreign proteins.

(4) The collected sediment fractions were mixed and stirred in 100 ml of sodium formate (0.05 normal). By centrifugation (3,000 rpm×30 min) floating fractions containing tissue thromboplastin were collected.

(5) To the collected floating fractions containing about 100 ml of tissue thromboplastin, 50 mM buffer agent for stabilizing the pH (phosphoric acid buffer solution, barbital buffer solution or tris buffer solution may be also usable), preservatives (0.1% w/v sodium azide), and stabilizer (0.1% calcium chloride) were mixed, and in order to make the coagulation reaction more manifest, in addition, a reagent was mixed, such as 0.5% polyethylene glycol (molecular weight 20,000) or 0.1% dextran (molecular weight 200,000). Furthermore, using sodium hydroxide of 0.1 normal, the pH was adjusted in the range of 7.20 to 7.50, and the salt was mixed to adjust the electric conductivity in the range of 6.5 to 10.0 mS, and glucose was added to adjust the osmotic pressure to 350 to 700 mOsm/kg.

(6) The thus obtained reagent containing tissue thromboplastin was freeze-dried and stored.

The effect of removing blood components and foreign proteins by treating the acetone powder is explained. Before extracting the tissue thromboplastin, the acetone powder was dissolved in solution, and in order to investigate the effect of removing the blood components and foreign proteins, the deproteinized specimen (operation to wash acetone powder in acidic solution) and the control specimen (not deproteinized) were prepared, and using these PT reagents, ten measurements each were compared. As a result, as shown in Table 1, the deproteinized PT reagent was higher in coagulation activity than the control PT reagent without this treatment (that is, the coagulation time was shorter), and was superior in reproducibility.

It is hence known that the operation to wash the acetone powder in acidic solution prior to extraction of tissue thromboplastin is effective for enhancing the coagulation activity of the PT reagent and for obtaining results of higher precision.

TABLE 1

| | Coagulation time | Reproducibility (variation factor) |
|---|---|---|
| Deproteinized | 14.58 sec | 0.52% |
| Not deproteinized | 16.52 sec | 1.86% |

Figure 3:
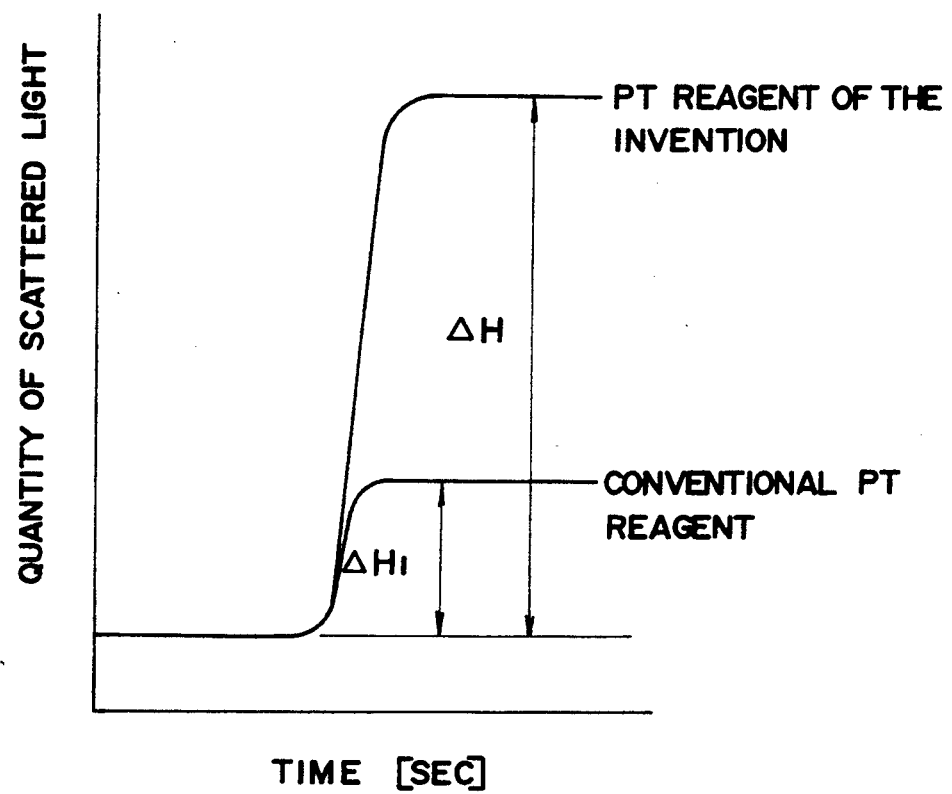
FIG. 3 is a graph showing the relation between the quantity of scattered light and time in a reagent for coagulating blood of the invention and a conventional reagent for coagulating blood not a containing high molecular substance.

Moreover, in order to see the effect of mixing a high molecular substance in the reagent, the PT reagent containing tissue thromboplastin blended with a high molecular substance and the PT reagent containing tissue thromboplastin without blend were prepared, and their coagulation curves were compared. As a result, as shown in FIG. 3, the PT reagent with high molecular substance was greater in the quantity of change of scattered light as compared with the PT reagent without the blend ($\Delta H > \Delta H_1$).

It is hence known that the coagulation reaction can be analyzed more closely and precisely by mixing a high molecular substance to with the PT reagent. As the high molecular substance, ethylene glycol with a molecular weight of 20,000 was used, and the blending rate was 0.5 w/v %. Meanwhile, $\Delta H$ denotes the change of scattered light by adding a high molecular substance, and $\Delta H_1$ represents the change of scattered light without a high molecular substance.

Figure 4:
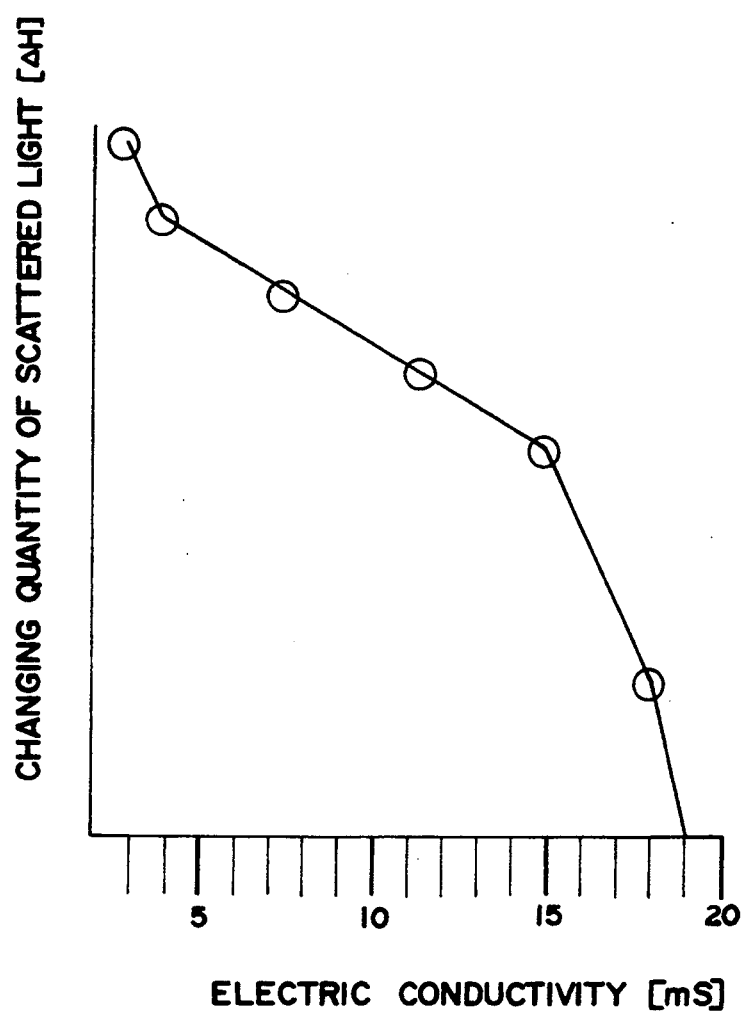
FIG. 4 is a graph showing the relation between the electric conductivity and change of scattered light.

FIG. 4 shows the effect of adjusting the electric conductivity in the range of 4.0 to 15.0 mS. To investigate the effect of adjusting the electrical conductivity of the PT reagent in the range of 4.0 to 15.0 mS, salt was added to the tissue thromboplastin, and the PT reagent was prepared so that the electrical conductivity be in the range of 2.0 to 20.0 mS. Using these PT reagents the plasma coagulation was measured, and the mean of the changing quantity of scattered light (the mean of ten measurements each) was compared. As a result, as shown in FIG. 4, although the changing quantity of scattered light tended to decline as the electrical conductivity was elevated, there was a stabilizing tendency between 4.0 and 15.0 mS.

Hence, by adjusting the electric conductivity of the PT reagent in the range of 4.0 to 15.0 mS, it is known that a stable change of scattered light may be obtained even if the electrical conductivity varies depending on the plasma to be measured, while maintaining a high level of change of scattered light.

Figure 5:
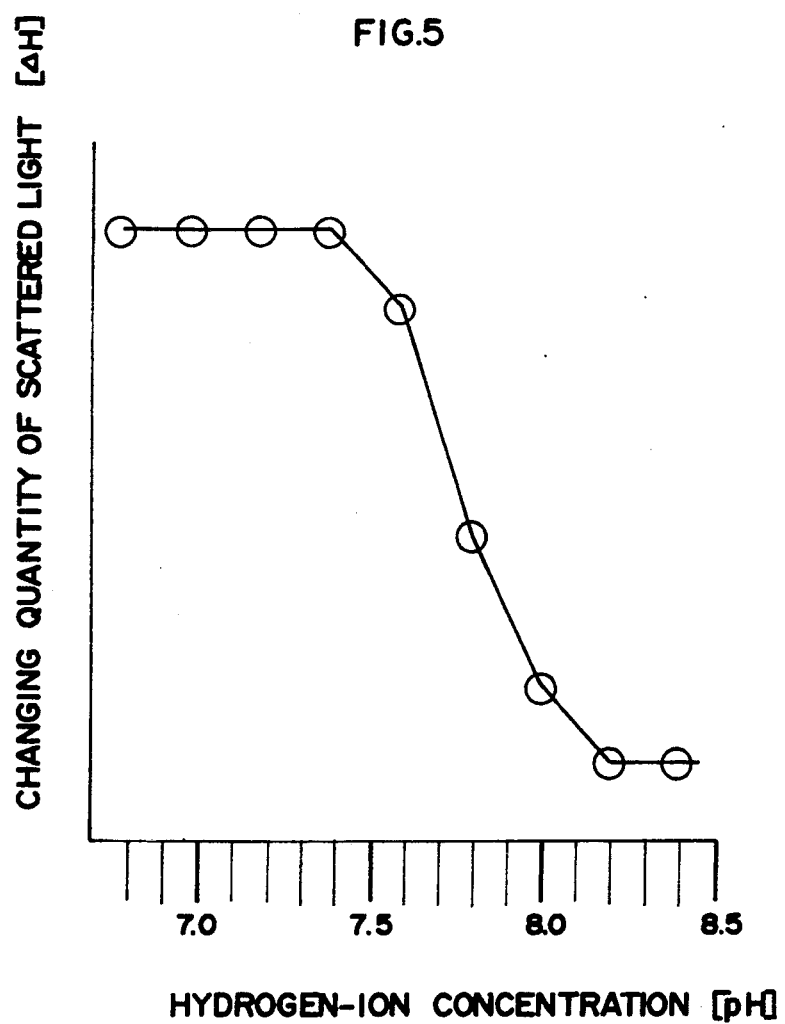
FIG. 5 is a graph showing the relation between pH and the change of scattered light.

FIG. 5 shows the effect of adjusting the pH in the range of 6.7 to 8.2, or preferably in the range of 7.2 to 7.5. To investigate the effect of adjusting the pH of the PT reagent in the range of 6.7 to 8.2, or preferably in the range of 7.2 to 7.5, PT reagents were prepared in a pH range of 6.7 to 8.5 by using hydrochloric acid of 1 normal and sodium hydroxide of 1 normal in a tissue thromboplastin extract, and the plasma coagulation was measured by using these PT reagents. The mean of the changing quantity of scattered light (the mean of ten measurements each) was compared. As a result, as shown in FIG. 5, at the pH in the range of 6.7 to 7.5, the changing quantity of the scattered light tended to be stable at a relatively high level, but between a pH of 7.5 and 8.2, as the pH elevated, the changing quantity of scattered light tended to decline, and at a pH of 8.2 or higher, the changing quantity of scattered light tended to be stable at a relatively low level.

Hence, by adjusting the pH of the PT reagent within 6.7 to 8.2, or preferably in the range of 7.2 to 7.5, it is known that a stable changing quantity of scattered light is obtained regardless of pH fluctuations depending on plasma specimens, while maintaining the changing quantity of scattered light at a high level.

Figure 6:
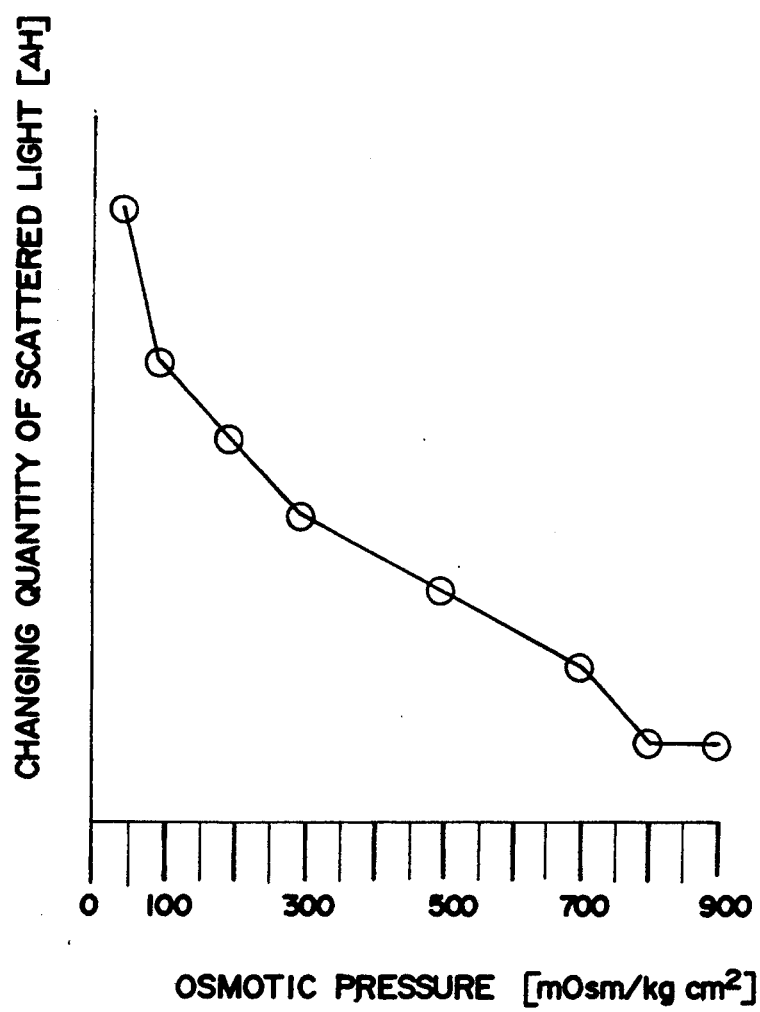
FIG. 6 is a graph showing the relation between the osmotic pressure and the change of scattered light.

FIG. 6 shows the effect of adjusting the osmotic pressure in the range of 100 to 700 mOsm/kg, or preferably in the range of 350 to 700 mOsm/kg. To see the effect of adjusting the osmotic pressure of the PT reagent in the range of 100 to 700 mOsm/kg, or preferably in the range 350 to 700 mOsm/kg, glucose was mixed to a tissue thromboplastin extract, and reagents were prepared by adjusting the osmotic pressure in a range of 50 to 900 mOsm/kg. Using these PT reagents, the plasma coagulation was measured, and the mean of the changing quantity of scattered light at that time (the mean of ten measurements each) was compared. As a result, as shown in FIG. 6, the changing quantity of scattered light tended to decline along with the elevation of osmotic pressure, but at the osmotic pressure in the range of 100 to 700 mOsm/kg, or in particular in a range in the range of 350 to 700 mOsm/kg, the changing quantity of scattered light tended to be stable.

Hence, by adjusting the osmotic pressure of the PT reagent in the range of 100 to 700 mOsm/kg, or preferably in the range of 350 to 700 mOsm/kg, it is possible to obtain a stable changing quantity of scattered light regardless of fluctuations of the osmotic pressure depending on specimen plasma, while maintaining the changing quantity of scattered light at a high level.

The reagent for coagulating blood of the invention possesses reactivity to coagulation factors, the same as the conventional coagulation factor activating reagent, and contains high molecular substance, and therefore it is effective to increase the turbidity change along with blood coagulation. By properly setting the conditions such as electrical conductivity, the polymerization reaction from fibrin monomers to fibrin polymer can be encouraged, and it is also effective to increase the turbidity change along with blood coagulation.

These facts suggest that the formation state of fibrin lumps as the final product of blood coagulation is firm, and therefore in the measuring apparatus on the basis of the principle of detection of viscosity, the detectable range is extended even if the fibrinogen quantity is small, while the demerit of being influenced by intensity of magnetic substance or the like may be solved. In the turbidity detection method, the changing quantity of transmitted light or scattered light increases, so that a more accurate detection may be realized.

The description herein relates to the field of blood coagulation, but the method and reagent for adjusting the coagulation reaction environments and making the reaction manifest are not limited to the reagent used in the coagulation factor activating substance disclosed in the invention, but may be applied to everything that reacts to solidify or coagulate physically.

What is claimed is:

1. A blood coagulating reagent that causes an increase in turbidity changes when added to a plasma sample, comprising:
   a substance activating coagulation factor selected from the group consisting of tissue thromboplastin, phospholipid and thrombin,
   calcium ion, and
   a high molecular substance with a molecular weight of at least 1000 for complicating intertwinement of fibrin fibers in a final stage of a coagulating reaction, wherein electrical conductivity is adjusted in the range of 4.0 to 15.0 mS, pH is adjusted in the range of 6.7 to 8.2 and osmotic pressure is adjusted in the range of 100 to 700 mOsm/kg.

2. A blood coagulating reagent of claim 1, wherein the high molecular substance is at least one selected from the group consisting of polyethylene glycol polyvinyl alcohol, polynoxyline, agarose, soluble starch, glycogen, dextran and dextrin.

3. A blood coagulating reagent of claim 1, wherein the substance activating coagulation factor is a fraction containing tissue thromboplastin extracted from acetone treated powder obtained by treating mammal tissues with acetone.

4. A blood coagulating reagent of claim 1, wherein the substance activating coagulation factor is a fraction containing phospholipid extracted from acetone treated powder obtained by treating mammal tissues with acetone.

5. A blood coagulating reagent of claim 1, wherein the substance activating coagulation factor is a fraction containing thrombin refined from mammal plasma.

6. A blood coagulating reagent of claim 3, wherein the fraction containing tissue thromboplastin is obtained dissolving acetone treated powder in solution, mixing, stirring, and centrifuging.

7. A blood coagulating reagent of claim 3, wherein the fraction containing tissue thromboplastin is obtained by floating acetone treated powder in acidic solution, centrifuging the solution to remove blood components and foreign proteins, adding solution for extracting a sediment fraction, stirring, and centrifuging said solution for extracting.

8. A blood coagulating reagent of claim 6, wherein the acidic solution comprises hydrochloric acid water.

9. A blood coagulating reagent of claim 7, wherein the acid solution comprises hydrochloric acid water and the solution for extraction comprises a solution containing sodium formate.

10. A blood coagulating reagent of claim 7, wherein the acid solution comprises hydrochloric acid water and the solution for extraction comprises a solution containing sodium acetate.

11. A blood coagulating reagent of claim 1, wherein the reagent is freeze-dried.

12. A blood coagulating reagent of claim 1, wherein the content of the high molecular substance is 0.25 to 2.0 (w/v)%.

* * * * *

UNITED STATES PATENT AND TRADEMARK OFFICE
CERTIFICATE OF CORRECTION

PATENT NO. : 5,401,663
DATED : March 28, 1995
INVENTOR(S) : Masaru Yonemura

It is certified that error appears in the above-indentified patent and that said Letters Patent is hereby corrected as shown below:

Col. 10, line 5, a "," should be inserted between "glycol" and "poly-".

Col. 10, line 22, "by" should be inserted after "obtained".

Signed and Sealed this

Thirteenth Day of June, 1995

Attest:

BRUCE LEHMAN

Attesting Officer

Commissioner of Patents and Trademarks